United States Patent [19]

Maier

[11] Patent Number: 5,308,616

[45] Date of Patent: May 3, 1994

US005308616A

[54] **MUTANT STRAIN OF *BRADYRHIZOBIUM JAPONICUM***

[75] Inventor: Robert J. Maier, Ellicott City, Md.

[73] Assignee: The Johns Hopkins University, Baltimore, Md.

[21] Appl. No.: 563,171

[22] Filed: Aug. 6, 1990

[51] Int. Cl.[5] .................. A01N 63/00; C12N 1/00; C12N 1/20; C05F 11/08

[52] U.S. Cl. ...................... 424/93 D; 435/252.1; 435/252.2; 435/252.3; 435/822; 71/7

[58] Field of Search ............... 435/252.1, 252.2, 252.3, 435/822; 424/93 D; 71/7

[56] References Cited

U.S. PATENT DOCUMENTS

| | | | |
|---|---|---|---|
| 4,803,165 | 2/1989 | Appelbaum | 435/252.2 |
| 4,818,696 | 4/1989 | Appelbaum et al. | 435/252.2 |
| 4,863,866 | 9/1989 | Zablotowicz et al. | 435/172.1 |
| 5,021,076 | 6/1991 | Kuykendall et al. | 435/252.2 |

FOREIGN PATENT DOCUMENTS

| | | | |
|---|---|---|---|
| 0164245 | 12/1985 | European Pat. Off. | 435/252.2 |
| 0164992 | 12/1985 | European Pat. Off. | 435/252.3 |

OTHER PUBLICATIONS

Bulen, William A., J. Bacteriology, 1961, 82:130–134.

*Primary Examiner*—David M. Naff
*Assistant Examiner*—Deborah K. Ware
*Attorney, Agent, or Firm*—Cushman, Darby & Cushman

[57] ABSTRACT

The present invention relates to mutant strains of *Bradyrhizobium japonicum* that are characterized in an increased nitrogen fixation rate and an altered molybdenum metabolism. The mutant strains require higher levels of molybdate than wild-type *Bradyrhizobium japonicum* for expression of nitrate reductase activity. In addition, the mutant strains express free-living nitrogenase activity in medium treated to remove molybdate, where the wild-type require molybdate supplementation.

6 Claims, 3 Drawing Sheets

MUTANT STRAIN OF *BRADYRHIZOBIUM JAPONICUM*

The present invention is concerned with a novel mutant strain of *Bradyrhizobium japonicum* which is characterized by increased symbiotic $N_2$ fixation rates and altered Mo metabolism properties.

BACKGROUND OF THE INVENTION

Studies on nodulated soybean plants have indicated that the lack of molybdenum (Mo) can limit biological $N_2$ fixation, as Mo supplementation can increase the rate of symbiotic $N_2$ fixation (see references 4, 11, 14, 16 identified hereinafter). The abundance of Mo in the earth's crust is only at an average concentration of about 15 $\mu$moles/Kg (22). Accordingly, it is unlikely that soil organisms such as legumes and their associated "root nodule" bacteria will commonly encounter high levels of Mo. Specific high affinity systems for Mo-sequestering would, therefore, be useful, especially in acidic soil environments where Mo is not readily available to the organism, and it would seem likely that $N_2$-fixing bacteria possess efficient mechanisms for scavenging trace levels of Mo.

High affinity molybdate sequestering processes have been described for $N_2$-fixing *Klebsiella pneumoniae* (12, 13, 25), *Clostridium pasteruianum* (5), and free-living (20), and bacteroid forms of *B. japonicum* (17). From these studies, it is clear that many $N_2$-fixing bacteria, even wild type *Bradyrhizobium japonicum* harbored in root nodules of soybean, have excellent Mo-sequestering abilities. Some nitrogenase systems are independent of the need for Mo (15), but it is not yet known if this is true for $N_2$-fixing systems of any of the rhizobia.

The metabolic processes between Mo sequestering and insertion into nitrogenase apparently involve several steps (10, 13, 25), including internalization from the free molybdate pool, and the synthesis of intermediates such as the iron molybdenum cofactor (25, 27). Studies thus far have implicated several Mo-binding intermediates prior to Mo bound in nitrogenase for several $N_2$-fixing bacteria (10, 21, 25) and at least 5 genes have been assigned roles in intracellular Mo metabolism in *K. pneumoniae* (13, 24-26). Most and perhaps all of these Mo-metabolizing genes are present in the symbiotic $N_2$-fixing bacterium *B. japonicum* as well (2, 26). For *B. japonicum* bacteroids, Mo is taken up by a high affinity process that is dependent on a transmembrane proton gradient (17). The Mo that is taken up by bacteroid suspensions in 1 min. is tightly associated with the cell, as most of it is not exchangeable with a 100-fold greater amount of exogenously-added Mo (17).

Mutants of *B. japonicum* in Mo metabolism and free-living $N_2$-fixation have previously been isolated (20). Some of the mutant strains appeared to be deficient in early Mo metabolism steps (such as binding Mo extracellularly) and other strains in later, presumably intracellular, Mo metabolism processes. Even though the phenotype of the mutants with respect to $N_2$-fixation was the primary interest, all of the mutants were isolated on the basis of the ability of added Mo to restore the activity of nitrate reductase, another Mo-containing enzyme.

SUMMARY OF THE INVENTION

The invention is directed to two mutant strains, identified as JH 359 and JH 310, that were isolated in the original screening process (20) but were not described previously and whose phenotype with respect to $N_2$ fixation is very different from other previously described mutant strains. These new strains are dependent on high levels of Mo for expression of nitrate reductase, but have much higher free-living nitrogenase activities in Mo-deficient conditions than the parent strain. Results from greenhouse studies also demonstrate that one of these mutants, strain JH359, has greater symbiotic $N_2$ fixation rates than the parent strain.

DETAILED DESCRIPTION OF THE INVENTION

The invention is described in more detail hereinafter including reference to FIGS. 1, 2, 3A, 3B, 4 and 5 which graphically illustrate various aspects of the invention. Except as otherwise indicated, conventional procedures were used to prepare, isolate, identify and test the mutant strains of the invention.

BRIEF DESCRIPTION OF THE DRAWINGS

The Figures illustrate the following:

FIG. 3. Double reciprocal plots of rate of Mo uptake versus Mo concentration for strains JH (●) and JH359 (○).

Figure 1:
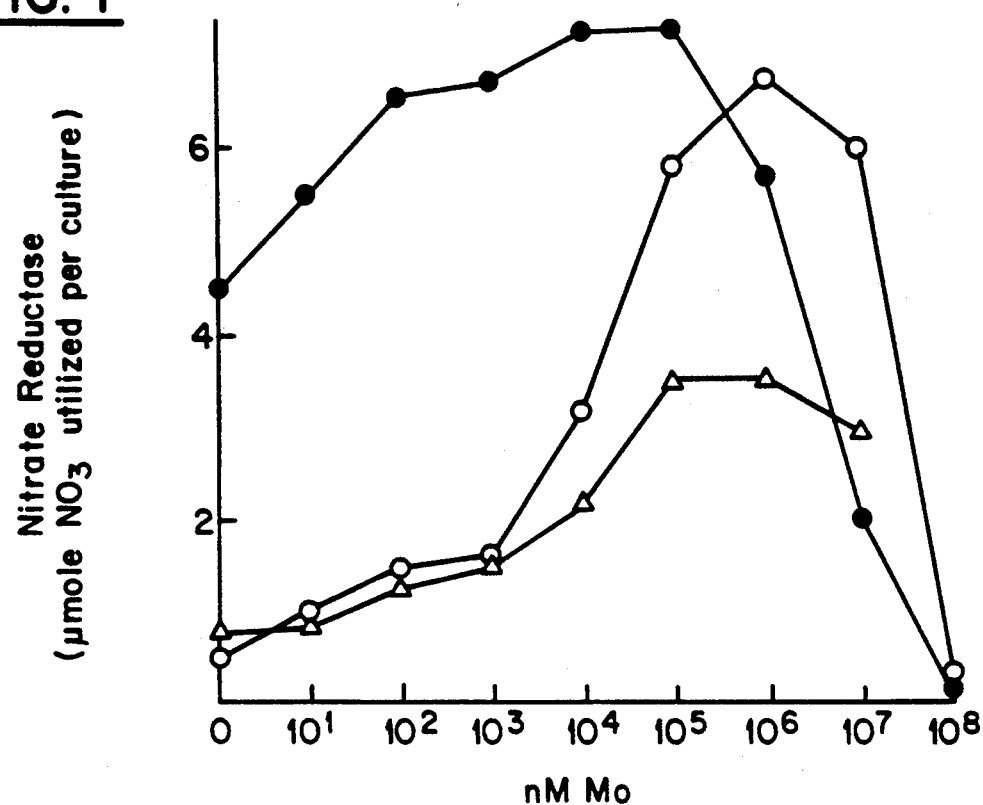
FIG. 1. Nitrate reductase activity as a function of Mo concentration by nitrogenase-derepressed cultures of wild-type JH (●), JH359 (○) and JH310 (△).

Literature cited by reference number hereinafter is more fully described as follows:

1. Agarwal, A. K. and D. L. Keister. 1983. Physiology of explanta nitrogenase activity in *Rhizobium japonicum*. Appl. Environ. Microbiol. 45: 1592-1601.
2. Bothe, H., F. J. deBruijn and W. E. Newton (eds.). Nitrogen Fixation: Hundred Years After. Proceed. 7th Internat'l Congress on Nitrogen Fixation. G. Fischer, Stuttgart. 1988.
3. Cataldo, D. A., M. Haroon, L. E. Schrader and V. L. Youngs. 1975. Rapid colorimetric determination of nitrate in plant tissue by nitration of salicylic acid. Commun. Soil Sci. Plant Anal. 6: 71-80.
4. Coventry, D. R., J. R. Hirth, T. G. Reeves and V. F. Burnett. 1985. Growth and nitrogen fixation by subterrenean clover in response to inoculation, molybdenum application, and soil amendment with lime. Soil Biol. Biochem. 17: 791-796.
5. Elliot, B. B. and L. E. Mortenson. 1975. Transport of molybdate by *Clostridium pasteurianum*. J. Bacteriol. 124: 1295-1301.
6. Eskew, D. L., R. M. Welch, and E. E. Cary. 1984. A simple plant nutrient solution purification method for effective removal of trace elements using controlled pore glass-8-hydroxyquinoline chelation column chromatography. Plant Physiol. 76: 103-105.
7. Graham, L. and R. J. Maier. 1987. Variability in molybdenum uptake activity in *Bradyrhizobium japonicum* strains. J. Bacteriol. 169: 2555-2560.

8. Graham, L., L. Stults and R. J. Maier. 1984. Nitrogenase-hydrogenase relationships in *Rhizobium japonicum*. Arch. Microbiol. 140: 243–246.
9. Hales, B. J. and E. E. Case. 1987. Nitrogen fixation by *Azotobacter vinelandii* in tungsten-containing medium. J. Biol. Chem. 262: 16205–.
10. Hinton, S. M. and L. E. Mortenson. 1985. Regulation and order of involvement of molybdoproteins during synthesis of molybdoenzymes in *Clostridium pasteurianum*. J. Bacteriol. 162: 485–493.
11. Huang, C. Y. 1979. The responses of soybean plants to molybdenum treatment, Taiwania 24: 38–46.
12. Imperial, J., R. A. Ugalde, V. K. Shah, and W. J. Brill. 1985. Mol− mutants of *Klebsiella pneumoniae* requiring high levels of molybdate for nitrogenase activity. J. Bacteriol. 163: 1285–1287.
13. Imperial, J., R. A. Ugalde, V. K. Shah, and W. J. Brill. 1984. Role of the nifO gene product in the incorporation of molybdenum into nitrogenase in *Klebsiella pneumoniae*. J. Bacteriol. 158: 187–194.
14. Janssen, K. A. and M. L. Vitosh. 1974. Effect of lime, sulfur Mo on nitrogen fixation and yield of dark red kidney beans. Agron. J. 66: 736–739.
15. Joerger, R. D. and P. E. Bishop. 1988. Bacterial alterntive nitrogen fixation systems. CRC Crit. Rev. Microbiol. 16: 1–14.
16. Lavy, T. L. and S. A. Barber. 1963. A relationship between yield responses of soybeans to Mo application and Mo content of seed produced. Agron. J. 55: 154–155.
17. Maier, R. J. and L. Graham. 1988. Molybdate transport by *Bradyrhizobium japonicum* bacterioids. J. Bacteriol. 170: 5613–5619.
18. Maier, R. J. and S. M. Hom. 1985. $H_2$ uptake negative (Hup−) mutants of *Rhizobium japonicum* and their use in the isolation of hup genes. Methods Enzymol. 118: 528–537.
19. Maier, R. J. and D. M. Merberg. 1982. *Rhizobium japonicum* mutants that are hypersensitive to repression by $H_2$ uptake by oxygen. J. Bacteriol. 150: 161–167.
20. Maier, R. J., L. Graham, R. G. Keefe, T. Pihl and E. Smith. 1987. *Bradyrhizobium japonicum* mutants defective in nitrogen fixation and molybdenum metabolism. J. Bacteriol. 169: 2548–2554.
21. Pienkos, P. T. and W. J. Brill. 1981. Molybdenum accumulation and storage in *Klebsiella pneumoniae* and *Azotobacter vinelandii*. J. Bacteriol. 145, 743–751.
22. Pope, M. T., E. R. Steel and R. J. P. Williams. 1989. The comparison between the chemistry and biochemistry of molybdenum and related elements. p. 3–40. In M. Coughlan (ed.). Molybdenum and Molybdenum-containing Enzymes. Pergamon Press. Oxford.
23. Riddle, G. P., J. G. Simmons, R. J. Hales and H. D. Breymer. 1982. Nitrogen fixation system of tungsten resistant mutants of *Azotobacter vinelandii*. J. Bacteriol. 152: 72–79.
24. Roberts, G. P., T. MacNeil, D. MacNeil and W. J. Brill. 1978. Regulation and characterization of protein products coded by nif (nitrogen fixation) genes of *Klebsiella pneumoniae*. J. Bacteriol. 136: 267–279.
25. Shah, V. K., R. A. Ugalde, J. Imperial and W. J. Brill. 1984. Molybdenum in nitrogenase. Ann. Rev. Biochem. Annual Reviews, Inc. Palo Alto, Calif. 53: 231–237.
26. Triplett, E. W., G. P. Roberts, P. W. Ludden and J. Handelsman. 1989. What's New in Nitrogen Fixation? ASM News 55: 15–21.
27. Ugalde, R. A., J. Imperial, V. K. Shah and W. J. Brill. 1985. Biosynthesis of the iron-molybdenum cofactor and the molybdenum cofactor in *Klebsiella pneumoniae*: Effect of sulfur source. J. Bacteriol. 164: 1081–1087.

EXAMPLE

Strain JH is a previously described rifampin-resistant derivative of *B. japonicum* USDA I110 (8). Free-living $N_2$-fixation characteristics of strain JH have also been described (8,20).

The strains JH359 and JH310 of the invention were obtained from strain JH by transposon Tn5 mutagenesis (18) and screening for growth on $No_3$-containing medium with and without Mo as described for obtaining other Mo metabolism mutants of *B. japnocium* (20). Genomic digests with EcoRi show that both strains JH 359 and JH310 contain a single Tn5 insertion in an approximately 12–14 kb size fragment (including the transposon). The procedures used to probe and genomic digest correspond to those described previously (20). All assays, Mo transport (7,17,20), nitrogenase activities (8,20), as well as inoculation and growth of soybean plants (7,17) and symbiotic $N_2$ fixation activities (7,17) were also carried out as previously described in the literature. Mo was also removed from growth medium as described previously (6,20) using precautions to keep Mo contamination to a minimum (17,20).

Nitrate Reductase Assays

Nitrate reductase activity was determined in cells that were first grown in Mo-deficient LOKG media (1). The cells were then harvested and suspended to $3 \times 10^8$ cells per ml in fresh LOKG containing 10 mM $KNO_3$ and the indicated Mo concentration (see FIG. 1). After 24 h in nitrogenase derepression conditions (1,8), the cells were removed and the supernatant solution assayed for $NO_3$ as described previously (3,20) by the method of salicylic acid nitration. The results represent the amount of $NO_3$ utilized in the 24 h period. Each point in FIG. 1 represents the average of three independent replicate derepression bottles.

Free-living Nitrogenase Activities

The medium for nitrogenase induction was LOKG, as described by Agarwal and Keister (1). Cultures grown in LOKG lacking Mo (20) to a cell density of about $2 \times 10^8$ cells per ml were dispensed (6 ml) into 250 ml acid washed serum bottles. The bottles were sealed with a rubber serum stopper, and the cultures incubated in an atmosphere of $CO_2$ (0.5%), $O_2$ (0.1%) and balance of Ar (19). Two percent $C_2H_2$ was added and the cultures incubated for 48 h as described (8, 20). Sodium molybdate was added as 0.1 ml amount to the 6 ml cell suspension at the start of the 48 h induction period. Nitrogenase was assayed by determining ethylene production over the 48 h period as described (20). For inhibition by tungsten, the cultures received 1 μM $Na_2MoO_4^=$ plus the indicated level of tungsten as sodium tungsten prior to the 48 h induction period. Each point in the figures (FIG. 2 or 5) is the average of three independent cultures.

Molybdenum Transport and Accumulation Assays

All assays were done as essentially described previously (17, 20). Free-living cells incubated in nitrogenase induction conditions (1,8) for 48 h without Mo (at about $2 \times 10^8$ cells per ml) received $Na_2^{99}MoO_4^=$ as described previously (20). They received 0.01, 0.02, 0.03, 0.05, 0.1 and 0.2 μM Mo (20) (composed of both radioactive and carrier, see 20). The cultures were allowed to continue shaking for 20 min. at which time three 0.5 ml samples were removed and the cells rapidly filtered and washed on the filter as described previously (20). After drying, the filters were counted (20) in Aquasol 2 scintillation fluid (New England Nuclear), and the Mo-uptake rate calculated (20). Bacteroids were harvested (7, 17) from six week old soybean plants. Mo uptake in 1 min at various Mo concentrations was determined on 30-34 mg (wet weight) per ml bacteroids. The washed bacteroids of strains of JH and JH359 were suspended in 0.05M potassium phosphate, pH 7.0. Mo was added (radioactive plus carrier) to initiate the (1 min) assay and the molybdate concentrations tested were 0.02, 0.025, 0.035, 0.05 and 1.0 μM (17). Two samples (0.25 ml each) were removed and the bacteroids rapidly filtered (7, 20) to determine the amount of cell-associated Mo as described (7). For Mo accumulation by bacteroids of strains JH and JH359, 8 ml of 30-34 mg (wet) weight of bacteroid suspension received 1.5 mCi $^{99}$Mo (0.032 nmol) supplied as carrier-free $Na_2MoO_4=$ and then four replicate 0.25 ml samples were removed at the times indicated to determine the level of cell-associated label. The total pmoles accumulated by the 8 ml culture was then calculated and shown in FIG. 4.

Inoculation and Growth of Soybeans

All conditions (growth of inoculant bacteria, plant cultivar and germination procedure, inoculation, nutrient solution composition, watering regime, plant growth conditions) were as described previously (7). The plants grown in Mo deficient conditions received N-free Jensen's solution of which the major components had been treated to remove Mo and ultrapure components were used (7). The plants receiving Mo received 1 mg sodium molybdate per pot of 5 plants weekly at weeks 1-4, thus they received a total of 4 mg sodium molybdate. The pots (15 pots for each strain and each Mo condition) were arrranged in a completely randomized design in the greenhouse after inoculation. The plants were harvested at the end of five weeks of growth, the plant tops removed and weighed, and root sections containing nodules (0.11 to 0.41 g fresh weight nodules per assay) were placed into 60 ml serum vials for quantitation of acetylene reduction activity (7). The amount of nodules per vial were most (and sometimes all if all nodules were associated with the crown area) of the nodules from an individual plant. Each value in the following Table 1 is based on 50 assays (plants). Further details as to the above procedures are described in the literature referenced herein (7, 17).

TABLE 1

Nitrogen Fixation (Acetylene Reduction) and Plant Fresh Weight of Soybeans Inoculated with Strains JH and JH359

| Strain | Acetylene reduction* | | Plant fresh weight (g) | |
|---|---|---|---|---|
| | +Mo | −Mo | +Mo | −Mo |
| Experiment 1 | | | | |
| JH | 10.4 ± 3.0 | 10.0 ± 2.5 | 6.6 ± 1.4 | 5.4 ± 1.2 |
| JH359 | 14.4 ± 2.3 | 13.0 ± 1.9 | 8.9 ± 1.4 | 7.9 ± 1.2 |
| Experiment 2 | | | | |
| JH | 8.8 ± 1.7 | 9.4 ± 1.2 | 5.7 ± 1.1 | 4.6 ± 1.0 |
| JH359 | 13.2 ± 2.1 | 12.7 ± 4.1 | 8.2 ± 1.6 | 7.3 ± 1.9 |

*(μmol $C_2H_4$ produced per h per g of nodule)

According to Student's t-test, the results (both acetylene reduction and fresh weight) for the mutant are significantly greater than the wild type at the 97.5% (Expt. 1) and 99% (expt. 2) levels of confidence. Fifty plants of each strain and each Mo condition were assayed for each of the two experiments.

RESULTS

After transposon Tn5 mutagenesis and plating on $NO_3$ containing medium as described previously (20) colonies were chosen that grew on $NO_3$ medium with 5 mM Mo (as sodium molybdate but poorly on media treated to remove Mo. This screening procedure was successfully used to isolate several classes of previously described mutants (20). Two strains not described previously, JH359 and JH310, were dependent on added Mo for nitrate reductase (see FIG. 1), as expected in light of the screening procedure used to detect the mutants. Both strains had dramatic increases in $NO_3$ reductase activities in liquid culture in the range of 0.1 to 1.0 mM molybdate, whereas the wild-type nitrate reductase activity did not respond markedly to Mo addition compared to the no-Mo-added condition. Strain JH359 expressed 12-fold greater $NO_3$ reductase activity in 1 mM Mo than in unsupplemented medium. The wild-type activity level was 4.5 μmole $NO_3$ utilized in the media treated to remove Mo and increased only to 7.3 μmole in 0.1 mM Mo. It is not surprising that the wild type is able to express $NO_3$ reductase in media treated to remove Mo. The catalytic efficiency of $NO_3$ reductase is generally high (25), so that even trace levels of Mo could result in sufficient active enzyme for $NO_3$ reduction catalysis.

Figure 2:
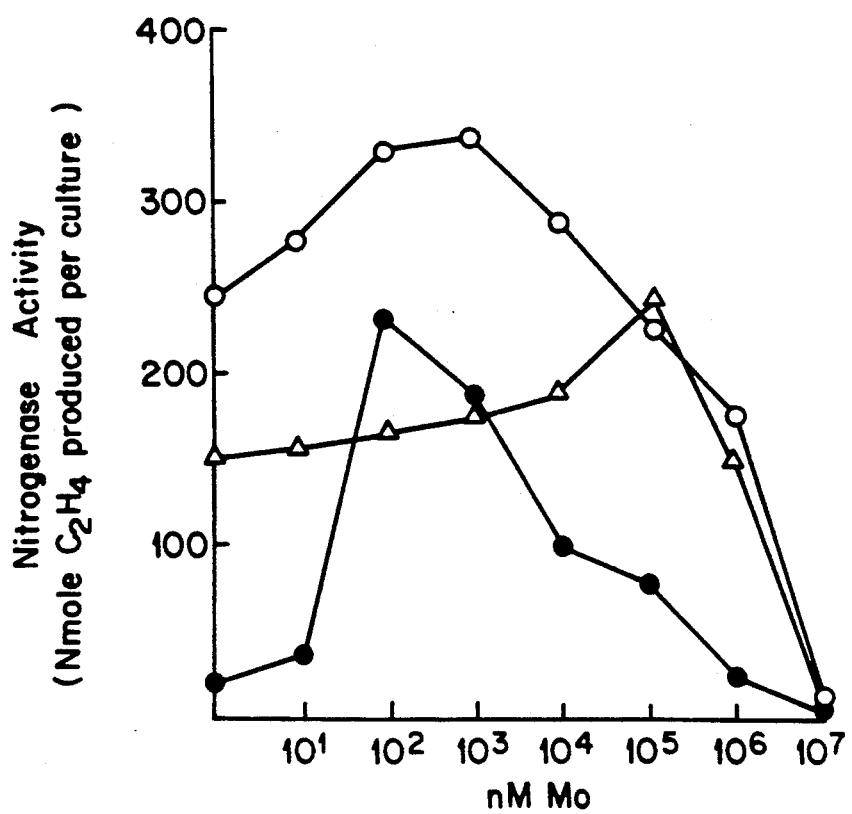
FIG. 2. Free-living nitrogenase activity as a function of Mo concentration for strains JH (●), JH359 (○), and JH310 (△).

Optimal nitrogenase activities in free-living *B. japonicum* strain JH require the addition of 100 nM Mo (20). Most of the previously isolated Mo-metabolism mutants of *B. japonicum* had phenotypes similar to those displayed by JH359 and JH310 (FIG. 1) for nitrate reductase activity. However, the strains studied previously were also dependent on up to 10 mM levels of added Mo for optimal free-living nitrogenase activity and they required higher levels of Mo than the wild-type, for both $NO_3$ reductase and nitrogenase. However, in contrast to the previously studied mutants and in contrast to the wild-type, the present strains JH310 and JH359 expressed substantial levels of nitrogenase activity even in the medium without added Mo (FIG. 2). Nitrogenase activity increased with added Mo in these mutants, but the level of activity was not nearly as dependent on added Mo as in the wild-type strain JH. From the results of FIGS. 1 and 2, it appears that these mutant strains require higher levels of Mo than the wild-type for optimal nitrate reductase activity, but much less Mo than the wild-type for substantial nitrogenase activity.

Strains JH359 and JH310 were found to have similar phenotypes, but strain JH359 has the most pronounced difference from the wild-type in its dependence on Mo for both enzyme activities.

Figure 3A:
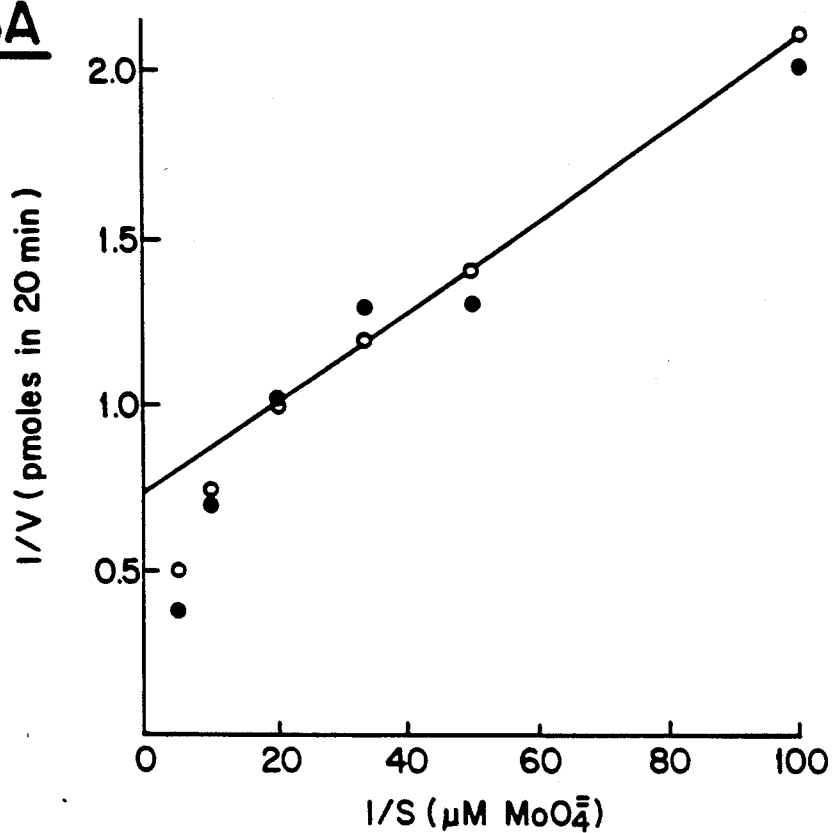
FIG. 3A) Free-living cells after derepression for nitrogenase in Mo-deficient medium.
Figure 3B:
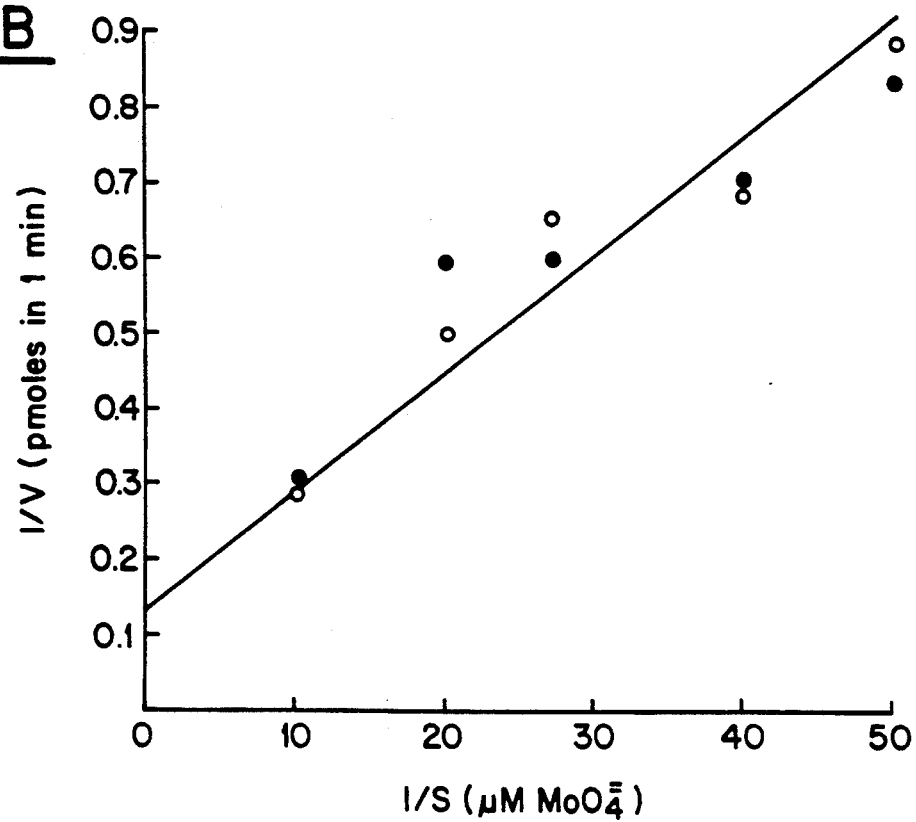
FIG. 3B) Bacteroids from soybeans grown in Mo-deficient conditions.
Figure 4:
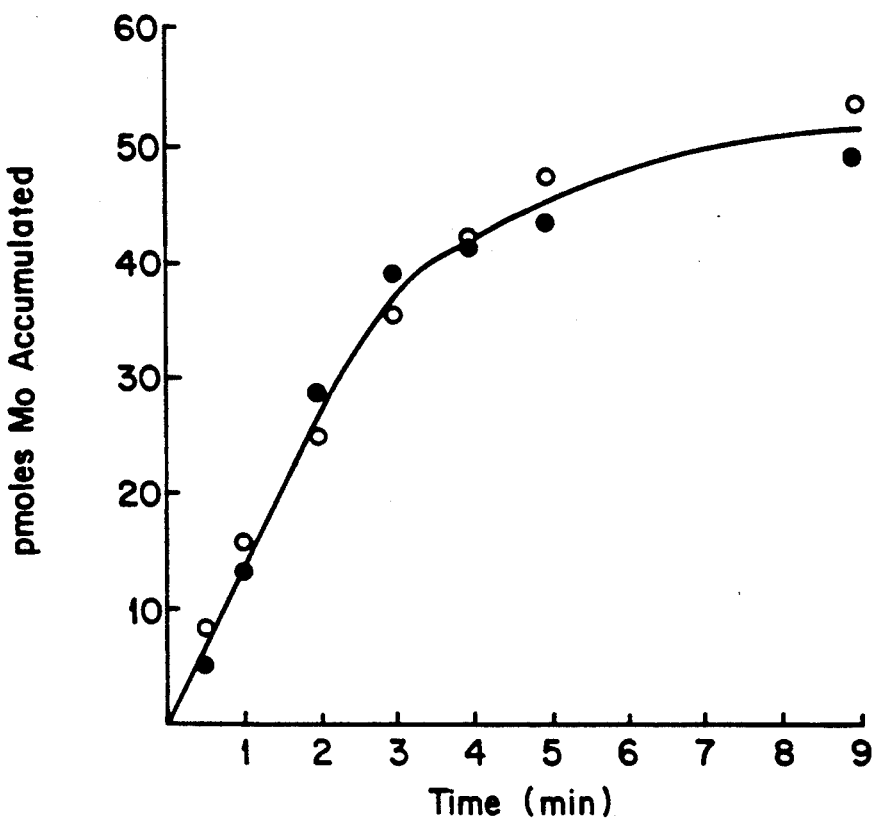
FIG. 4. Mo accumulation by bacteroids from soybeans in Mo-deficient conditions. JH (●), JH359 (○).

Differences in phenotypes expressed in Mo-metabolism mutants of *B. japonicum* might be attributed in part to the affinity of whole cells for Mo (20). In free-living culture, the wild-type strain JH expressed a higher and lower affinity Mo uptake binding system as determined from double reciprocal plots of Mo uptake versus Mo concentration (20). Some previously-described mutants lacked the high affinity component. The ability of strain JH359 to express nitrogenase activity in Mo-deficient medium could be due to superior Mo-binding ability, i.e. a superior high-affinity component. It is also possible that in the medium treated to remove MO, JH359 could scavenge trace levels of Mo so that nitrogenase could function at nearly optimal (as in Mo-supplemented) conditions. Accordingly, Mo-binding assays were performed to determine the affinity of Mo-starved JH359 cells for Mo. Free-living cells (FIG. 3A) contained high and low affinity binding components, consistent with previous results (the line in FIG. 3A is drawn only through the higher affinity-associated points). The results (FIGS. 3A and B) showed that both free-living and bacteroid cells of JH359 had approximately the same affinity for Mo as the wild-type. Therefore, the phenotype of JH359 cannot be attributed to an alteration in affinity for Mo. Additionally, the ability of bacteroid suspensions (from Mo-deprived plants) to sequester and steadily accumulate Mo from a low Mo environment (about 4 nM Mo) is the same for both JH wild-type and JH359 (FIG. 4). Both strains had initially rapid accumulation rates (for the first 3 min) and slower rates as the Mo was apparently internalized.

Figure 5:
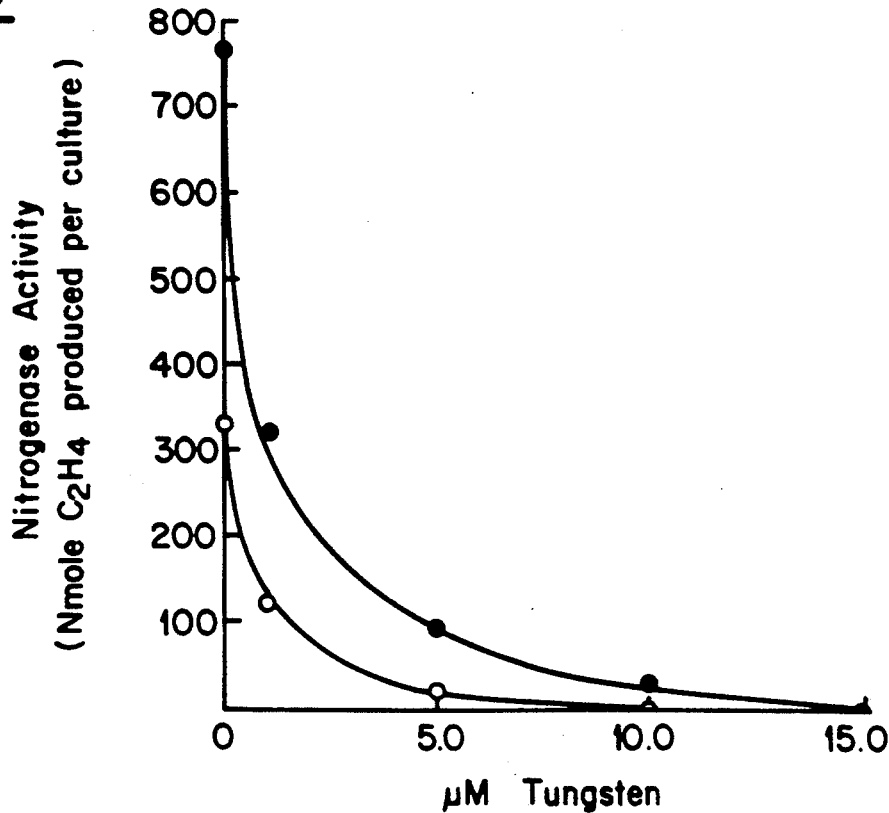
FIG. 5. Inhibition of nitrogenase activity expression by tungsten in free-living cultures of wild-type JH (○) and mutant strain JH359 (●).

Free-living nitrogenase activity in the mutant strain JH359 is not highly dependent on added Mo, and nitrogenase activity in Mo-deficient medium is considerably higher than the activity in the wild-type. This activity may be due to a Mo-independent nitrogenase. Tungsten is thought to be able to substitute for Mo in Mo-containing enzymes such as nitrate reductase and nitrogenase (25). Tungsten can become incorporated into the iron-molybdenum cofactor of nitrogenase when *A. vinelandii* is derepressed for nitrogenase in medium containing 1 to 10 mM tungstate (9). Tungsten tolerant mutants of *A. vinelandii* have been isolated that grow and fix $N_2$ in the presence of $Na_2WO_4$ (15). Some of these mutants did not express the protein subunits of the usual nitrogenase components, but expressed other $NH_4$-repressible proteins even in the presence of 1 µM $Na_2MoO_4$. The results led to the discovery of an alternative Mo-independent set of $N_2$ fixation proteins and genes (15). Similarly, Riddle et al (23) isolated an *A. vinelandii* mutant strain able to grow in N-free Mo-deficient medium in the presence of 10 mM $WO_4^{-2}$. They concluded that their mutant expressed an altered nitrogenase able to operate with or without Mo in the presence of W. It is possible that strain JH359 expresses a Mo-independent, W-tolerant $N_2$ fixation system. Therefore, the wild-type and JH359 were derepressed for nitrogenase in the presence of both Mo and W (FIG. 5). Nitrogenase expression for both strains was strongly inhibited by tungstate. Accordingly, the activities of both strains is apparently due to a conventional Mo-containing nitrogenase.

The symbiotic properties of strain JH359 have been compared with JH. In two greenhouse experiments, soybeans inoculated with the mutant JH359 and grown in either Mo-supplemented or Mo-deficient conditions had greater specific $N_2$ fixation rates, and significantly greater plant fresh weight than plants inoculated with the wild-type strain (Table 1). In Mo-deficient conditions, the acetylene reduction rates and plant fresh weights were found to be up to 35% and 58% greater, respectively, for the mutant than wild-type nodulated plants. Five week old plants inoculated with the mutant and grown in N-free, Mo-depleted medium were clearly larger than wild-type inoculated plants. Other experiments have also shown clearly better growth of soybeans inoculated with JH359 compared to wild-type inoculated plants. The alteration in Mo-metabolizing properties of JH359 has a positive effect on symbiotic $N_2$ fixation rates and ultimately on soybean growth. Presumably this is due to higher $N_2$ fixation.

The foregoing shows that mutant strains JH359 and JH310 have been isolated by the use of a procedure that was used previously to isolate Mo metabolism mutants that were also deficient in $N_2$ fixation. However, the new strains according to the invention have higher free-living nitrogenase activities in low Mo conditions than the wild-type. The apparently efficient use of Mo for $N_2$ fixation in these mutants does not appear to be correlated to more efficient Mo accumulation, transport or Mo scavenging systems but seems to correlate with a poor ability to utilize available Mo for another Mo-enzyme, nitrate reductase. It appears likely that both Mo sinks, nitrogenase and nitrate reductase, are normally in competition with each other for Mo, especially in low Mo conditions. It is possible then that JH359 has a lesion in Mo processing for nitrate reductase, so that more of the internalized Mo is then available for nitrogenase. In this regard, it is clear that nitrate reductase function requires some processing steps involving Mo that are separate from nitrogenase Mo processing functions, at least in enterics (12, 25, 27). On the other hand, it is also possible that JH359 has nitrogenase activity which is independent of Mo. Such Mo-independent nitrogenases have been described for *Azotobacter vinelandii* and *Azotobacter chroococcum*, but could presumably occur in other bacteria as well (15). The similar inhibition patterns of nitrogenase activity with tungsten for the wild-type and strain JH359 suggest that in both strains it is a conventional Mo-containing nitrogenase that is operative.

The mutation in JH359 results in increased symbiotic $N_2$ fixation rates and greater plant growth in greenhouse conditions. This effect was observed even when the plants were supplied with molybdenum. It may be that even the Mo-supplemented plants had insufficient Mo to suppress the phenotype of JH359. In any case, since JH359 contains a single Tn5 insertion and displays altered free-living nitrogenase and nitrate reductase activities with respect to Mo levels, the superior symbiotic phenotype is probably also due to a change in some aspect of intracellular Mo metabolism.

In summary, the foregoing shows that the new mutant strains of *B. japonicum* obtained after transposon Tn5 mutagenesis require higher levels of molybdate than the wild-type for growth on $NO_3$ containing medium. These mutant strains expressed more than 5-fold greater $NO_3$ reductase activities in the range of 0.1 to 1.0 mM added molybdate compared to non-Mo-supplemented medium, whereas the wild-type (JH) nitrate reductase activity was not markedly influenced by Mo supplementation. Mutant strains JH310 and JH359 expressed substantial free-living nitrogenase activity even in medium treated to remove molybdate, and free-living nitrogenase activity was influenced little by Mo supplementation, whereas the wild-type required 100 nM added Mo for highest nitrogenase activity. Double reciprocal plots of Mo uptake rates versus Mo concentration show that both bacteroids and free-living cells of mutant strain JH359 have about the same affinity for Mo as the parent strain. Bacteroids of both the mutant and wild-type also had similar Mo accumulation rates over a 9 min period in very low Mo (4 nM) conditions. Free-living nitrogenase activity for strain JH359 and the wild-type were both strongly inhibited by tungsten. Thus the nitrogenase activities of both strains is apparently due to a conventional Mo-containing nitrogenase.

Soybeans inoculated with JH359 and grown in either Mo-supplemented or Mo-deficient conditions had greater specific acetylene reduction rates, and significantly greater plant fresh weight than plants inoculated with the wild-type strain. In Mo-deficient conditions, the acetylene reduction rates and plants fresh weights were up to 35% and 58% greater, respectively, for mutant compared to wild-type nodulated plants.

It will be recognized that the invention is not limited to any particular theory or explanation as to the manner in which the present mutants function, the scope of the invention being defined in the following claims wherein:

We claim:

1. A strain of *Bradyrhizobium japonicum* which is selected from the group consisting of *B. japonicum* ATCC 55447 and *B. japonicum* ATCC 55448, said *B. japonicum* strain has increased nitrogenase activity in the absence of Mo when compared with the wild-type parent strain and containing a single Tn5 insertion in an approximately 12–14 kb size fragment.

2. The strain *B. japonicum* ATCC 55447 according to claim 1.

3. The strain *B. japonicum* ATCC 55448 according to claim 1.

4. In a method of $N_2$ fixation, the improvement which comprises inoculating a plant with strain ATCC 55447 or ATCC 55448 of *Bradyrhizobium japonicum*, said strain having increased nitrogenase activity in the absence of Mo when compared with the wild-type parent strain and containing a single Tn5 insertion in an approximately 12–14 kb size fragment.

5. The method of claim 4 carried out in an Mo-supplemented environment.

6. The method of claim 4 carried out in an Mo-depleted environment.

* * * * *